US00PP10583P

United States Patent [19]

Bergman

[11] Patent Number: Plant 10,583

[45] Date of Patent: Sep. 1, 1998

[54] HIBISCUS PLANT NAMED 'GULF WIND'

[75] Inventor: Wendy R. Bergman, Lehigh Acres, Fla.

[73] Assignee: Yoder Brothers, Inc., Barberton, Ohio

[21] Appl. No.: 807,404

[22] Filed: Feb. 27, 1997

[51] Int. Cl.[6] ..... A01H 5/00

[52] U.S. Cl. ..... Plt./67.8

[58] Field of Search ..... Plt./67.8

*Primary Examiner*—James R. Feyrer

*Attorney, Agent, or Firm*—C. A. Whealy

[57] ABSTRACT

A new and distinct cultivar of Hibiscus plant named 'Gulf Wind', characterized by its very dark green leaves; upright and outwardly spreading, uniform and symmetrical plant habit; freely flowering, large and numerous light golden yellow-colored flowers with dark red throats; long peduncles; good resistance to flower bud abscission; and excellent postproduction longevity.

2 Drawing Sheets

The present invention relates to a new and distinct cultivar of Hibiscus, botanically known as *Hibiscus rosa-sinensis*, and hereinafter referred to by the cultivar name 'Gulf Wind'.

The new cultivar is a product of a planned breeding program conducted by the inventor in Alva, Fla. The objective of the breeding program is to create new Hibiscus cultivars having uniform plant habit, early flowering, numerous flowers per lateral branch, desirable flower color, resistance to flower bud abscission, and good postproduction longevity.

The new cultivar originated from a cross made by the inventor in Alva, Fla. of the nonpatented commercial cultivar 'Euterpe' as the female, or seed, parent with the commercial cultivar 'Waikiki ' (disclosed in U.S. Plant Pat. No. 7,834) as the male, or pollen, parent. Compared to plants of the light orange-colored cultivar 'Euterpe', plants of the new Hibiscus have larger flowers and are more resistance to flower bud abscission. In addition, plants of the cultivar 'Euterpe ' have lobed leaves whereas plants of the new Hibiscus do not have lobed leaves. Compared to plants of the pink-colored cultivar 'Waikiki', plants of the new Hibiscus have larger flowers.

The cultivar 'Gulf Wind' was discovered and selected by the inventor as a flowering plant within the progeny of the stated cross in a controlled environment in Alva, Fla., on Oct. 4, 1993. The selection of this plant was based on its desirable flower color, resistance to flower bud abscission, good postproduction longevity, and uniform plant habit and flowering.

The new Hibiscus is similar to plants of the nonpatented cultivar 'Sundance'. In side-by-side comparisons conducted in Alva, Fla., plants of the new cultivar differ from plants of the cultivar Sundance in the following characteristics:

1. Plants of the new Hibiscus are more freely branching than plants of the cultivar Sundance.
2. Plants of the new Hibiscus have more flowers than plants of the cultivar Sundance.
3. Plants of the new Hibiscus have lighter golden yellow-colored flowers than plants of the cultivar Sundance.
4. Plants of the new Hibiscus flower about 10 days earlier than plants of the cultivar Sundance.

Asexual reproduction of the new cultivar by terminal cuttings taken in a controlled environment in Alva, Fla., has shown that the unique features of this new Hibiscus are stable and reproduced true to type in successive generations.

The cultivar 'Gulf Wind' has not been observed under all possible environmental conditions. The phenotype may vary somewhat with variations in environment such as temperature, light intensity, nutrition and water status without, however, any variance in genotype.

The following traits have been repeatedly observed and are determined to be the unique characteristics of 'Gulf Wind'. These characteristics in combination distinguish 'Gulf Wind' as a new and distinct cultivar:

1. Very dark green leaves.
2. Uptight and outwardly spreading, uniform and symmetrical plant habit.
3. Freely flowering, large and numerous light golden yellow-colored flowers with dark red throats.
4. Long peduncles.
5. Good resistance to flower bud abscission.
6. Excellent postproduction longevity.

The accompanying colored photographs illustrate the overall appearance of the new cultivar, showing the colors as true as it is reasonably possible to obtain in colored reproductions of this type.

The first photograph comprises a side perspective view of typical plant of 'Gulf Wind'.

The second photograph comprises a close-up view of a typical flower of 'Gulf Wind'.

Flower and foliage colors in the photographs may appear different from the actual colors due to light reflectance.

The aforementioned and following observations, measurements, values, and comparisons describe plants grown in Alva, Fla., in 15-cm containers with day temperatures ranging from 16 to 35°C and night temperatures ranging from 10 to 24°C. Plants were grown under a polypropylene covering with light levels ranging from 6,000 to 9,000 footcandles.

In the following description, color references are made to The Royal Horticultural Society Colour Chart except where general terms of ordinary dictionary significance are used.

Botanical classification: *Hibiscus rosa-sinensis* cv. 'Gulf Wind'.

Parentage:

*Male or pollen parent.*—*Hibiscus rosa-sinensis* cv. 'Waikiki ' (U.S. Plant Pat. No. 7,834).

*Female or seed parent.*—*Hibiscus rosa-sinensis* cv. 'Euterpe' (not patented).

Propagation:

*Type.*—By terminal cuttings.

*Time to develop roots.*—About 28 days at temperatures of 24°C.

*Rooting habit.*—Moderately vigorous, thick and well-branched.

Plant description:

*Plant form and growth habit.*—Perennial, evergreen, upright and outwardly spreading, inverted triangle, uniform and symmetrical plant habit. Moderate vigor.

*Branching habit.*—Moderate, usually three lateral branches develop after removal of terminal apex.

*Plant height, soil level to top of flowers.*—About 25 cm.

*Plant diameter, area of spread.*—About 32 cm.

*Lateral branch description.*—Length: About 6 cm. Diameter: About 4.5 mm. Color: Immature: 200A to 146A. Mature: 199B.

Foliage description:

*Arrangement.*—Alternate, single.

*Leaf size, largest leaves.*—Length: About 9.5 cm. Width: About 6.25 cm.

*Leaf shape.*—Ovate.

*Leaf apex.*—Acute to rounded.

*Leaf base.*—Cordate.

*Margin type.*—Crenate to dentate.

*Texture.*—Glabrous and glossy on both surfaces.

*Aspect.*—Slightly undulating.

*Color.*—Young foliage, upper surface: 147A. Young foliage, lower surface: Greener than 146A. Mature foliage, upper surface: Very dark green, darker than 147A. Mature foliage, lower surface: 147A. Venation, upper surface: Darker than 147A. Venation, lower surface: 147A.

*Petiole.*—Length: About 3 cm. Diameter: About 3 mm. Texture: Pubescence on upper surface. Color: 146A to 200A.

Flower description:

*Natural flowering season.*—Usually spring and summer or during periods of warm weather.

*Flower arrangement.*—Flowers arranged singly at terminal leaf axils. Very freely flowering with usually five to seven flower buds and/or open flowers per terminal apex. Flowers flat and face upright. Flower appearance: Star-shaped single. Light golden yellow-colored petals with dark hot pink throat. Flowers are open for about one day before closing. Flowers persistent.

*Flower diameter.*—About 16 cm.

*Flower bud (just before opening).*—Rate of opening: About one day depending on temperatures. Length: About 7 cm. Diameter: About 1.5 cm. Shape: Columnar. Color: Golden with red overtones.

*Petals.*—Texture: Satiny, smooth. Arrangement: Corolla consists of five petals that overlap. Shape: Spatulate with rounded apex. Margin: Entire. Size: Length: About 9.5 cm. Width: About 6.5 cm. Color: Upper surface: Light golden yellow, 20A/20B. Veins are dark red, 53B. Lower surface: Lighter golden yellow, 20B. Throat: Dark red, 53A/53B. After closing: Golden with red overtones.

*Sepals.*—Appearance: Six sepals fused into a star-shaped calyx. Shape: Linear. Texture: Smooth. Color, outer surface: 146A.

*Peduncles.*—Length: About 6 cm. Diameter: About 2 mm. Angle: Upright. Strength: Strong, rigid. Color: 146A.

*Reproductive organs.*—Androecium: Stamen number: Numerous. Stamen length: About 5 mm. Anther shape: Globular. Anther size: About 1 mm. Amount of pollen: Abundant. Pollen color: 21A. Gynoecium: Pistil length: About 10.5 cm. Style length: About 9 cm. Style color: Apex 46A to light pink. Base: 46A. Stigma shape: Round. Stigma diameter: About 2.5 mm. Stigma color: 46B. Ovary color: White.

Disease resistance: No known Hibiscus diseases observed to date on plants grown under commercial greenhouse conditions.

Seed production: If cross-pollinated, seed production may be observed. Usually one to twenty seeds per capsule.

It is claimed:

1. A new and distinct Hibiscus plant named 'Gulf Wind', as illustrated and described.

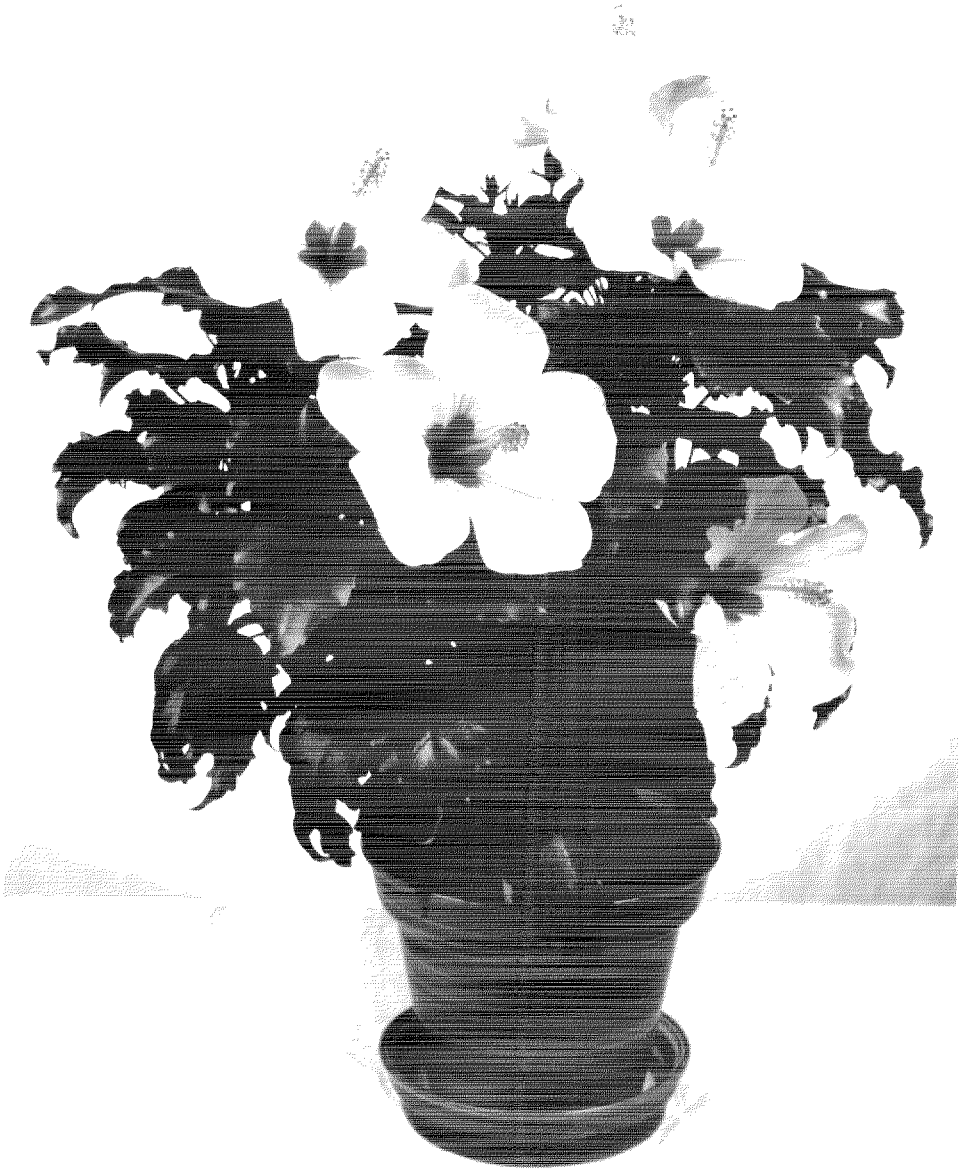

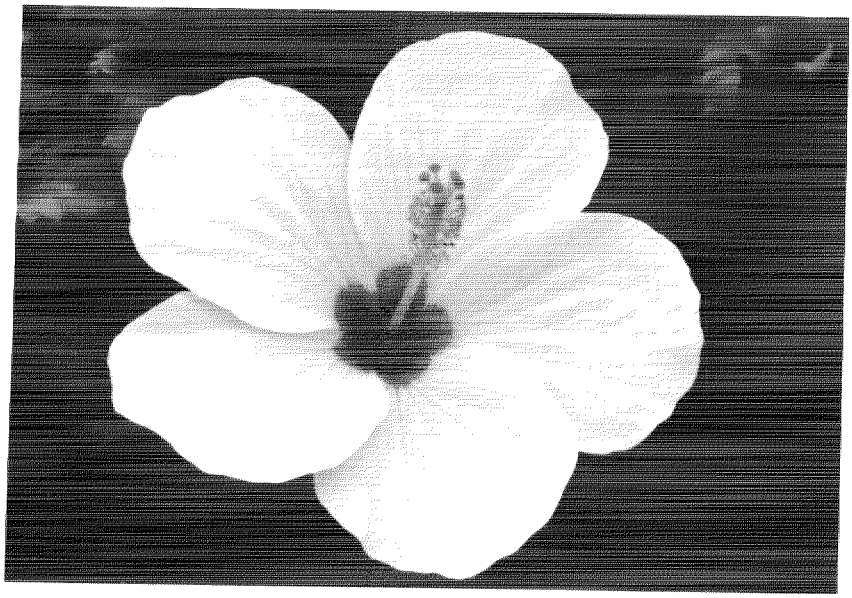

* * * * *